United States Patent [19]

Cometti et al.

[11] 4,439,618
[45] Mar. 27, 1984

[54] PROCESS FOR THE PREPARATION OF METHYL ESTERS OF ARYLPROPIONIC ACIDS OPTICALLY ACTIVE

[75] Inventors: Giuseppe Cometti, Verbania-Pallanza; Gian P. Chiusoli, Parma, both of Italy

[73] Assignee: Montedison S.p.A., Milan, Italy

[21] Appl. No.: 405,608

[22] Filed: Aug. 5, 1982

[30] Foreign Application Priority Data

Aug. 6, 1981 [IT] Italy ................... 23391 A/81

[51] Int. Cl.³ .............................................. C07C 69/76
[52] U.S. Cl. .................................... 560/56; 560/20; 560/21; 560/51; 560/100; 560/102; 560/105; 562/466; 562/406; 260/465 C
[58] Field of Search ............... 560/105, 20, 21, 51, 560/100, 102; 562/406, 466; 260/465 C

[56] References Cited

U.S. PATENT DOCUMENTS 3,530,168 9/1970 Biale et al. ................... 560/105
3,839,378 10/1974 Yamaguchi et al. ............ 560/105

FOREIGN PATENT DOCUMENTS 1249867 9/1967 Fed. Rep. of Germany ...... 560/105
2646792 4/1977 Fed. Rep. of Germany ...... 560/105
51-1070745 6/1976 Japan ............................. 560/105

Primary Examiner—Paul J. Killos

[57] ABSTRACT

Optically active methyl esters of arylpropionic acids are prepared by reaction of the corresponding vinylaromatic compounds with carbon monoxide and methyl alcohol in the presence of a palladium catalyst system consisting of a palladium compound associated with optically active diphenyl-neomenthylphosphine and with trifluoroacetic acid, at substantially atmospheric pressure and at a temperature comprised between 20° and 80° C. There is dealt with particular regioselective and enantioselective catalysis conditions.

The products obtained consist of esters of arylpropionic acids or of the corresponding acids obtainable from them, and are useful intermediates in the synthesis of organic compounds, particularly of pharmaceutical products.

17 Claims, No Drawings

PROCESS FOR THE PREPARATION OF METHYL ESTERS OF ARYLPROPIONIC ACIDS OPTICALLY ACTIVE

BACKGROUND OF THE INVENTION

The following formula (I) can be attributed to the methyl esters of arylpropionic acids obtainable according to the present invention:

wherein R stands for an aryl group, preferably a phenyl, diphenyl or a naphthyl group, also substituted with groups inert under the reaction conditions.

Processes for the preparation of arylpropionic acids esters are known in general. Thus, for instance, it is known to carbonylate styrene in the presence of ethyl alcohol and of palladium diphosphine complexes.

In this way there are obtained mixtures of ethyl 2- and 3-phenylpropionate in varying rates and, in some cases, also with remarkable selectivities, while the same cannot be said with regard to the enantioselectivity towards an optical isomer. Moreover, the parametric operational conditions of the reaction, 120° C. for 16 hours under a pressure of 200 Kg/sq.cm. of carbon monoxide, evidently appear less suited for an industrial application because of their drasticity.

Other processes foresee the carbonylation of the olefins in the presence of palladium complexes with ligands of the phosphoric, nitrylic, olefinic type and with atoms of halides (chlorine).

Nonetheless, also in this case, the results described as to the selectivity do not correspond to the results when tested from the enantioselectivity point of view, which constitutes the original aspect of the process conducted according to this invention.

Summing up, it may be generally maintained from the examination of the previously cited literature that, even if under more drastic conditions of temperature and carbon oxide pressure, it is possible to adjust in the desired direction the selectivity or, better still, the regioselectivity of the reaction within a rather wide range, making recourse to different types of catalysts and especially to different phosphines as the ligands for the palladium catalyst.

However, from the same literature it may be learned that the results of a good regioselectivity are not accompanied by equally good results from the point of view of the enantioselectivity, or at least there are not remarkable as possible equally good results.

OBJECTS OF THE INVENTION

The present invention concerns a process for the preparation of optically active methyl esters of arylpropionic acids of formula (I). In particular, the present invention concerns a catalytic process for the preparation of methyl esters of arylpropionic acids starting from vinylaromatic compounds and carbon monoxide.

Specifically, the present invention is directed to the synthesis of methyl esters of arylpropionic acids (I) by the carbonylation of vinylaromatic compounds, under conditions of regioselective and enantioselective catalysis, based on the use of a catalytic system consisting of special zero valent palladium or palladium (II) combinations with diphenylneomenthylphosphine and trifluoroacetic acid.

The products thereby obtained consist of the above indicated methyl esters of arylpropionic acids, which products, whether as such or in the form of the corresponding acids, which are easily obtainable from them by hydrolysis, etc. according to known methods, represent interesting compounds that may find a convenient use in the industrial synthesis of organic products in general, and particularly in the synthesis of pharmaceutical products.

In fact, for instance, according to the present invention, it is possible, starting from the suitable vinylaromatic compound, that is, from 2-vinyl-6-methoxynaphthyl, to prepare the 2-(6'-methoxy-2'-naphthyl)-propionic acid of the formula:

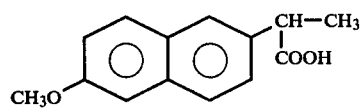

which finds an application in the pharmaceutical field as anti-inflammatory analgesical, anti-itching agent, etc. More particularly, according to the process object of this invention, it is possible to obtain the products in an optically active form with such an enantioselectivity as to make it unnecessary, in certain instances, to separate the optically active form from the racemic mixture from which the desired optical antipode is in any way always separable in the purest form by conventional separation methods, with active bases, etc.

The above mentioned compound is widely known, commercialized and described in the literature, as are likewise the corresponding pharmaceutical preparations in the form of solutions, suspensions, pills, capsules, etc.

THE PRESENT INVENTION

Thus, object of this invention is that of providing a process for the preparation of optically active methyl esters of arylpropionic acids (I) that is simple and economical and that is free from the drawbacks indicated in the discussion of the techniques of the Prior Art taken into consideration.

The process, according to this invention, consists in the reaction of a vinylaromatic compound with carbon monoxide and methylalcohol in the presence of a catalyst system comprising a palladium compound, the optically active diphenylneomenthylphosphine and trifluoroacetic acid, as later on better defined.

The present invention, therefore, provides a resolution of, or contribution to, the realization of a process that is capable of associating in the results a very high regioselectivity with a considerable enantioselectivity, which association actually represents the essential characteristic that definitely distinguishes the present invention, from the point of view of the results, from those obtainable according to the above discussed method of the Prior Art.

GENERAL DESCRIPTION OF THE INVENTION

According to the present invention there is provided a process for the preparation of methyl esters of arylpropionic acids of formula (I), and particularly with a high regioselectivity associated with a considerable asymmetric induction or enantioselectivity, characterized in that a vinylaromatic compound, in the following henceforth also called "substrate", having the formula (II):

$$R-CH=CH_2 \qquad (II)$$

wherein: R represents an aryl group, preferably chosen from amongst phenyl-, diphenyl- and naphthyl groups, in their turn possibly also substituted with groups that are inert under reaction conditions, is made to react with carbon monoxide and methyl alcohol, in the presence of a palladium catalyst, associated with the optically active diphenylneomenthylphosphine and in further presence of trifluoroacetic acid, under substantially atmospheric pressure and at a temperature comprised between 20° C. and about 80° C.

The process may be schematically represented by the following equation:

$$R-CH=CH_2 + CO + CH_3OH \xrightarrow[\text{diphenylneomenthyl-phosphine}]{Pd + F_3ac}$$

(II)

$$\begin{array}{c} R-CH-CH_3 \\ | \\ COOCH_3 \end{array}$$

(I)

In the other words, the vinylaromatic substrate (II) is made to react in a methanol medium with carbon monoxide in the presence of a Pd catalyst, further on more precisely defined, and particularly in the presence of trifluoroacetic acid and of the optically active phosphine diphenylneomenthylphosphine.

In this way there are obtained optically active arylpropionic esters displaying an optical purity which varies according to the type of substrate itself.

The Pd based catalyst preferably consists of a combination of Pd(O) with diphenylneomenthylphosphine; in the catalytic Pd(O) molecule there may possibly be present also other ligand compounds, such as for instance dibenzylidenacetone associated with the above said phosphine. Alternatively, the Pd catalyst may consist of salt combintions of PD(II) with carboxylic acids or of Pd acetylacetonate, in the presence of the above mentioned optically active phosphine.

To the Pd(O) catalyst with diphenylneomenthylphosphine there way be thus attributed the following general formula (III):

$$PdL_nL'_m \qquad (III)$$

wherein:
L represents the optically active diphenylneomenthylphosphine;
L' represents an olefinic ligand of the conjugated type containing electron-attracting groups such as methylmaleate, dibenzylidenacetone, benzylidenacetone;
n is an integer comprised between 1 and 3, while
m is an integer comprised between 0 and 2, such that n+m=3.

Catalysts of Pd(II) are, as indicated above, the salts of carboxylic acids or Pd acetylacetonate, preferably, always associated with the optically active phosphine.

Either catalytic Pd systems associated with the active phosphine are always used in the presence of trifluoroacetic acid.

Summing up, under the particular parametrical reaction conditions, the association of the optically active diphenylneomenthylphosphine with trifluoro-acetic acid and with palladium leads to unexpected results of a very high regioselectivity, unforeseeably combined with a considerable enantioselectivity. The use of other phosphines and/or of other acids has turned out in an insufficient regioselectivity and/or enantioselectivity.

This result must be considered so much the more unexpected as the asymmetric induction caused by the catalytic system described herein is assured in an acceptable degree only if the reaction is carried out within a narrow range of pressure values.

The increase of operational pressure, above the value of about 2 atm, leads to a fast drop in the optical activity.

The present invention may thus be considered to represent the overcoming of a prejudice deriving from the available Prior Art technique which, although using catalytic systems of Pd complexes with phosphines, which may find a reference to those of this invention, have not attained comparable enantioselectivities, and thus should have deterred the skilled in the Art from further researches in the field of such phosphinic Pd catalysts in order to obtain the unexpected improvements in the production achieved according to the present process.

As previously described, the vinylaromatic $R-CH=CH_2$ substrate (II) may consist in its aromatic part of a phenyl-, diphenyl- or naphthyl group.

Said groups may, however, in their turn contain substituent groups that are inert under reaction conditions, preferably chosen from amongst alkylic, alcoxylic, ketonic or ester groups, all having up to 4 carbon atoms, nitrilic, halogenhydric or nitric groups.

The reaction is conducted in the absence of a true and proper inert solvent; it is operated in the presence of an excess of methyl alcohol which serves as reaction medium.

Nonetheless, in the presence of particular substrates, it may prove useful to associate with the methyl alcohol varying quantities of organic solvents such as, for instance, alcohols (n-butanol) or ethers (anisol). Obviously, the use of alcohols as co-solvents will lead to the collateral formation of minor quantities of the corresponding esters.

The catalytic system consisting of PD(O) with the optically active diphenylneomenthylphosphine of formula (III) or of the Pd (II) salt and diphenylneomenthylphosphine associated with trifluoroacetic acid, is quantitatively definable according to the following reciprocal molar ratios: the molar ratio between Pd(O) catalyst of formula (III) and the trifluoroacetic acid is comprised between about 1:10 and 1:100; the molar ratios between the Pd (II) salt, the optically active diphenylneomenthylphosphine and the trifluoroacetic acid, are comprised between about 1:3:10 and 1:3:100.

With respect to the mols of substrate (II), there are used from 1:10 to 1:100 mols of a catalytic complex derived from Pd(O) of formula (III) or from Pd (II). Greater quantities of substrate are however compatible.

The temperature, as indicated above, is comprised between about 20° C. and about 80° C., but preferably is comprised between about 40° and 50° C., while the operational pressure is already the atmospheric pressure. Nevertheless, there may be used pressures also slightly higher, up to about 1–2 atmospheres.

The diphenylneomenthylphosphine is an intermediate compound available on the market and/or preparable according to known methods.

The reaction times may vary depending on the parametrical conditions and on the type of substrate (II), although, just as an order of magnitude there would already be sufficient times comprised between about 2 and 4 hours.

At the end of the reaction, the separation of the products is achieved by means of conventional methods such as, for instance, the distillation of the products or by chromatographic elution, etc., while the Pd may be recycled.

The operational procedures are very simple and in practice reduce themselves to bringing into contact the reactants in a carbon oxide atmosphere. It is also possible to operate in the presence of an inert atmosphere such as nitrogen, argon, etc.

According to an effective procedure, into a reactor, provided with a stirrer, a coolant and a thermometer, possibly kept in an inert nitrogen atmosphere, there is loaded the palladium compound complexed with the optically active phosphine of formula (III), or associated with the phosphine, together with substrate (II); thereupon there is admixed the methyl alcohol, the possible solvent and the trifluoroacetic acid, maintaining the desired quantities and ratios. One goes then on with the heating up to the pre-established temperature and for the pre-established time, after having substituted the nitrogen atmosphere with that of carbon monoxide.

At the end of the reaction, the reaction product is distilled under vacuum and the residue, containing the palladium, may be recovered and re-cycled with the same quantities of reactants, while the distilled ester is recovered and then, if necessary, separated by means of chromatography.

The process, thanks to the simple and mild operational conditions, proves particularly advantageous.

A particular advantage is represented by the high regioselectivity of the reaction associated with an equally interesting enantioselectivity, thus ensuring a pronounced operational fitness in the field of pharmaceutical compounds for which, as it is well known, the optical selectivity aspect is of the highest therapeutical and economical interest.

SPECIFIC DESCRIPTION OF THE INVENTION

The invention will now be described in further detail in the following examples, given, however, for illustrative purposes.

Example 4 is given for comparison purposes; it may be remarked from it that, when operating under pressure values higher than 2 atmospheres about, a lower optical purity is obtained.

EXAMPLE 1

Into a 100 cc flask, provided with a magnetic stirrer, a coolant and a thermometer, kept in an inert nitrogen atmosphere, and containing a solution of 0.4 g of palladium dibenzylidenacetone and 0.68 g of (+) diphenylneomenthylphosphine in 15 cc of styrene, there were admixed 15 cc of methanol and 3 cc of trifluoroacetic acid.

This reaction mixture was thereupon heated up to 50° C. for 4 hours, after previous substitution of the nitrogen atmosphere with a carbon monoxide atmosphere.

The resulting product was then distilled under vacuum. The palladium-containing residue may be further utilized for other carboxylation cycles with the same quantity of reactants. The thus distilled ester was then purified by means of thin-layer chromatography (eluent:ethylether:n-hexane 1:9) which yielded 0.64 g of a product formed by the methyl esters of 2-phenylpropionic acid (94%) and of the 3-phenylpropionic acid (6%), according to the gas-chromatographic analysis. The thus obtained product proved to be a non-racemic mixture of methyl 2-phenylpropionate having a 52% enantiomeric excess of the levorotary ester.

EXAMPLE 2

Under the same operational conditions as those described in example 1, to 0.3 g of palladium dibenzylidenacetone and to 0.5 g of (+) diphenylneomenthylphosphine dissolved in 5 cc of 4-chlorostyrene, were admixed 5 cc of methanol and 1 cc of trifluoroacetic acid.

Thereby, after distillation and separation, by means of chromatography on a silica gel plate, were obtained 0.32 g of methyl ester of 2-(4-chlorophenyl)propionic acid.

The ester thus obtained proved to be a non-racemic mixture having $[\alpha]_D^{24}$ −42,12 [CHCl$_3$; c=1].

EXAMPLE 3

Under the same operational conditions of example 1, to 0.32 g of palladium dibenzylidenacetone, 0.54 g of (+)neomenthyldiphenylphosphine and 3 g of 2-vinyl-6-methoxynaphthalene in 10 cc of anisol, there were additioned 10 cc of methanol and 2 cc of trifluoroacetic acid.

There was thus obtained, by distillation and separation, by means of chromatography on a silica gel plate, methyl 2-(6'-methoxy-2'-naphthyl)-propionate having a regioselectivity greater than 95%, and an enantiomeric excess of the levorotary ester of 43.8%; [CHCl$_3$; c=1].

EXAMPLE 4 (for comparative purposes)

Into a 100 cc autoclave, kept in an inert nitrogen atmosphere, there was loaded a mixture containing 0.27 g of palladium dibenzylidenacetone, 0.46 g of (+)neomenthyldiphenylphosphine, 15 cc of styrene, 15 cc of methanol and 3 cc of trifluoroacetic acid. Into the autoclave was then introduced carbon monoxide at room temperature to the extent of reaching a pressure of 35 atmospheres.

The reaction was then conducted for 4 hours at 50° C. After cooling down of the reaction mixture, this latter was discharged from the autoclave and the product was separated by following the procedures described in example 1. Thereby were obtained, with a regioselectivity of 100%, 0.7 g of methyl 2-phenyl-propionate having an enantiomeric excess of the levorotary ester of 15.6%; [CHCl$_3$; c=1].

What is claimed is:

1. A process for the regioselective and enantioselective preparation of methyl esters of arylpropionic acids, by carbonylation of the corresponding vinylaromatic compound, in the presence of palladium catalysts, characterized in that a compound having the formula (II):

 (II)

wherein R is selected from the group consisting of aryl radicals and aryl radicals substituted with groups that are inert under the reaction conditions, is made to react with carbon monoxide and with methyl alcohol in the presence of a palladium catalyst associated with the optically active diphenylneomenthylphosphine and in the further presence of trifluoroacetic acid, under a substantially atmospheric pressure and at a temperature comprised between 20° C. and 80° C. about.

2. A process according to claim 1, characterized in that the aryl group R is selected from the group consisting of phenyl-, diphenyl and naphthyl groups.

3. A process according to claim 1, characterized in that the aryl group is substituted by inert groups selected from the group consisting of alkyl-, alkoxyl-, ketonic, ester groups having from 1 to 4 carbon atoms, nitrilic, halogenhydric and nitric groups.

4. A process according to claim 1, characterized in that the palladium catalyst is selected from the group consisting of complex compounds of Pd(O) with the diphenylneomenthylphosphine, having formula (III):

$$PdL_nL'_m \qquad (III)$$

wherein:
L represents the optically active diphenylneomenthylphosphine;
L' represents an olefinic ligand of the conjugated type containing electron-attracting groups;
n is an integer comprised between 1 and 3;
m is an integer comprised between 0 and 2, such that n+m=3, associated with trifluoroacetic acid, and a Pd(II) salt of carboxylic acids and/or palladium acetylacetonate, associated with the optically active diphenylneomenthylphosphine and with the trifluoroacetic acid.

5. A process according to claim 4, characterized in that the olefinic ligand L' is selected from the group consisting of dibenzylidenacetone, benzylidenacetone and methylmaleate.

6. A process according to claim 1, characterized in that said process is conducted in a reaction medium selected from the group consisting of an excess of methyl alcohol and mixtures of methyl alcohol with organic solvents.

7. A process according to claim 6, characterized in that the solvent consists of methyl alcohol in admixture with a solvent selected from the group consisting of butyl alcohol and anisol.

8. A process according to claim 4, characterized in that the molar ratio between the Pd(O) complex of formula (III) and trifluoroacetic acid is comprised between about 1:10 and about 1:100.

9. A process according to claim 4, characterized in that the molar ratios between Pd(II) salt, the diphenylneomethylphosphine and the trifluoroacetic acid are comprised between about 1:3:10 and about 1:3:100.

10. A process according to claim 4, characterized in that the Pd salt is palladium acetylacetonate.

11. A process according to claim 1, characterized in that there are used from 1 to 100 mols of palladium catalyst per 1 mol of compound (II).

12. A process according to claim 1, characterized in that said process is conducted at a temperature comprised between about 40° C. and 50° C.

13. A process according to claim 1, characterized in that said process is conducted under a pressure comprised between atmospheric pressure and about 2 atmospheres.

14. A process according to claim 1, characterized in that said process is conducted in the presence of an inert gas.

15. A process according to claim 1, characterized in that said process is conducted in a reaction medium selected from the group consisting of alcohols and ethers.

16. A process according to claim 1, characterized in that said process is conducted in the presence of an inert gas selected from the group consisting of nitrogen and argon.

17. A process according to claim 2, characterized in that the aryl group is substituted by inert groups selected from the group consisting of alkyl, alkoxy, ketonic, ester groups having from 1 to 4 carbon atoms, nitrilic, halogenhydric and nitric groups.

* * * * *